United States Patent
Kato et al.

(10) Patent No.: US 6,318,178 B1
(45) Date of Patent: Nov. 20, 2001

(54) CLEANLINESS EVALUATION METHOD FOR METALLIC MATERIALS BASED ON ULTRASONIC FLAW DETECTION AND METALLIC MATERIAL AFFIXED WITH EVALUATION OF CLEANLINESS

(75) Inventors: Yoshiyuki Kato; Yoshio Nuri; Shoichi Takemoto, all of Himeji (JP)

(73) Assignee: Sanyo Special Steel Co., Ltd., Himeji (JP)

( * ) Notice: Subject to any disclaimer, the term of this patent is extended or adjusted under 35 U.S.C. 154(b) by 0 days.

(21) Appl. No.: 09/470,993

(22) Filed: Dec. 23, 1999

(30) Foreign Application Priority Data

| Jan. 20, 1999 | (JP) | 11-011969 |
| Apr. 27, 1999 | (JP) | 11-119789 |
| Nov. 12, 1999 | (JP) | 11-323246 |

(51) Int. Cl.[7] ............ G01N 29/04; G01N 29/10
(52) U.S. Cl. ............... 73/602; 73/620; 73/629
(58) Field of Search ............. 73/602, 598, 599, 73/600, 597, 620, 627, 606, 624, 625, 626, 628, 629

(56) References Cited

U.S. PATENT DOCUMENTS

| 3,712,119 | * | 1/1973 | Cross et al. | 73/67.7 |
| 4,412,453 | * | 11/1983 | Nagai et al. | 73/601 |
| 4,914,952 | * | 4/1990 | Miyajima et al. | 73/598 |
| 5,884,685 | * | 3/1999 | Umezawa et al. | 164/453 |
| 5,887,481 | * | 3/1999 | Leroy et al. | 73/866 |
| 5,955,673 | * | 9/1999 | Leroy et al. | 73/602 |

FOREIGN PATENT DOCUMENTS

| 10002344-A1 | * | 8/2000 | (DE) | 73/602 |
| 11271282-A | * | 10/1999 | (JP) | 73/602 |
| 2000310620-A | * | 11/2000 | (JP) | 73/602 |

* cited by examiner

*Primary Examiner*—Daniel S. Larkin
*Assistant Examiner*—Rose M. Miller
(74) *Attorney, Agent, or Firm*—Kanesaka & Takeuchi

(57) ABSTRACT

Cleanliness of a metallic material to be tested is provided. The method includes the steps of setting n inspection fields in predetermined portions of the metallic material to be tested, scanning each inspection field by ultrasonic flaw detection method for non-metallic inclusions in the metal thereby to determine the maximum non-metallic inclusion diameter $a_j$ (j=1,n), and calculating the estimated maximum non-metallic inclusion diameter $a_{max}$ in the metallic material to be tested from the maximum non-metallic inclusion diameter $a_j$ (j=1,n) determined for each inspection field, thereby evaluating the cleanliness of metallic materials quickly with high accuracy and high reliability.

17 Claims, 6 Drawing Sheets

※ QTM – Method : Quantitative Television Microscope Method

CLEANLINESS EVALUATION METHOD FOR METALLIC MATERIALS BASED ON ULTRASONIC FLAW DETECTION AND METALLIC MATERIAL AFFIXED WITH EVALUATION OF CLEANLINESS

BACKGROUND OF THE INVENTION

1. Field of the Invention

The present invention relates to a method for evaluating the cleanliness of metallic materials. More specifically, the present invention relates to a method for evaluating the cleanliness of a metallic material to be tested by scanning predetermined inspection fields of the metallic material under test by ultrasonic flaw detection method to obtain data on non-metallic inclusions (for example, oxide, nitride, sulfide, etc.) included therein, and calculating estimated maximum non-metallic inclusion diameter in the metallic material to be tested from these data with predetermined equations.

The present invention also relates to a metallic material affixed with the evaluation of cleanliness described above.

2. Description of the Related Art

Recently, with the advancement in the metallurgical technology, cleanliness of metallic materials such as steel has been greatly improved, so that non-metallic inclusions of medium to large sizes beyond 20 $\mu$m are rarely included in metallic materials and sizes of the non-metallic inclusions present have also been decreasing. In this trend, it is becoming very difficult to detect large inclusions that occur accidentally or with an extremely low probability.

There is no technique capable of evaluating and ensuring cleanliness of metallic materials practically to cope with such a situation as described above.

A method for testing cleanliness of metallic materials that is currently a standard practice employs optical microscope observation. However, the area that can be covered with this method is as small as 1000 mm$^2$, thus making the method utterly impractical for evaluating the cleanliness of metallic materials of high cleanliness as mentioned above (JIS G0555, ASTM E45, ASTMA 295, DIN 50602, ISO 4967, etc.).

On the other hand, such methods have been proposed that inclusions are extracted from a metallic material by acid dissolution with the particle size of the inclusion being evaluated under a microscope, or a metallic material is dissolved by Electron Beam Melting dissolution with the inclusions that float being observed under a microscope (Japanese Patent Application Laid-open No. Hei 9-125199, Japanese Patent Application Laid-open No. Hei 9-125200). However, in certain cases, as the inclusions dissolve into the acid or the inclusion itself fuses or coagulates, these methods also cannot be applied to the evaluation of cleanliness of metallic materials of high cleanliness.

The methods described above have also such a drawback as the inability to process quickly due to a long time required for the acid dissolution or other cause, and therefore are difficult to adapt to mass production processes.

In an industry where a metallic material of high cleanliness is processed as a raw material, strict machining processes are designed on the basis of assumption that the metallic material has a high cleanliness. When there are variations in the cleanliness of the metallic material, however, such problems as frequent occurrences of defective products result, thus leading to significant decrease in productivity.

In bearing steel, spring steel, steel to make power transmission shaft, gear steel and the like that bear high loads, for example, immature breakage may result from the presence of inclusions of sizes larger than a certain level. In such industries, therefore, there are demands for the supply of metallic materials that bear certification of high cleanliness thereof or that are guaranteed to have a certain level of cleanliness.

SUMMARY OF THE INVENTION

An object of the present invention is to provide a method for evaluating the cleanliness of metallic materials, which is capable of adapting to the advancements in metallurgical technology that have been achieved recently and the significant improvement in the cleanliness of metallic materials such as steel.

Another object of the present invention is to provide a method for quickly evaluating the cleanliness of metallic materials, which is capable of adapting to the mass production processes of such metallic materials.

Further another object of the present invention is to provide a metallic material affixed with the evaluation of cleanliness thereof in compliance with the significant improvement in the cleanliness of metallic materials such as steel due to the advancements in metallurgical technology achieved recently.

The present inventors started with such an assumption that maximum inclusion diameter in a metallic material determines the basic workability of the metallic material.

However, it is very difficult for the conventional methods employing optical microscopes to determine the maximum inclusion diameter in a metallic material of a lot size of 1 kg to 2 tons or greater lots (for example 2 to 200 tons).

The present inventors have been studying a method for estimating the maximum inclusion diameter in a metallic material to be tested by such a procedure as microscopic observation area is set to standard inspection area of $S_0=100$ mm$^2$, n=30 to 60 pieces of samples are taken, and extreme value statistics technique is applied to the maximum inclusion diameters determined for the samples. But this method is not sufficiently reliable for estimating such large inclusions as mentioned previously, and is not practical for evaluating the cleanliness of metallic materials.

The present invention provides means for solving the problems described above, and is briefly described as claims. The nature, principle and utility of the invention will become more apparent from the following detailed description with reference to the accompanying drawings.

DETAILED DESCRIPTION OF THE PREFERRED EMBODIMENTS

Figure 1:
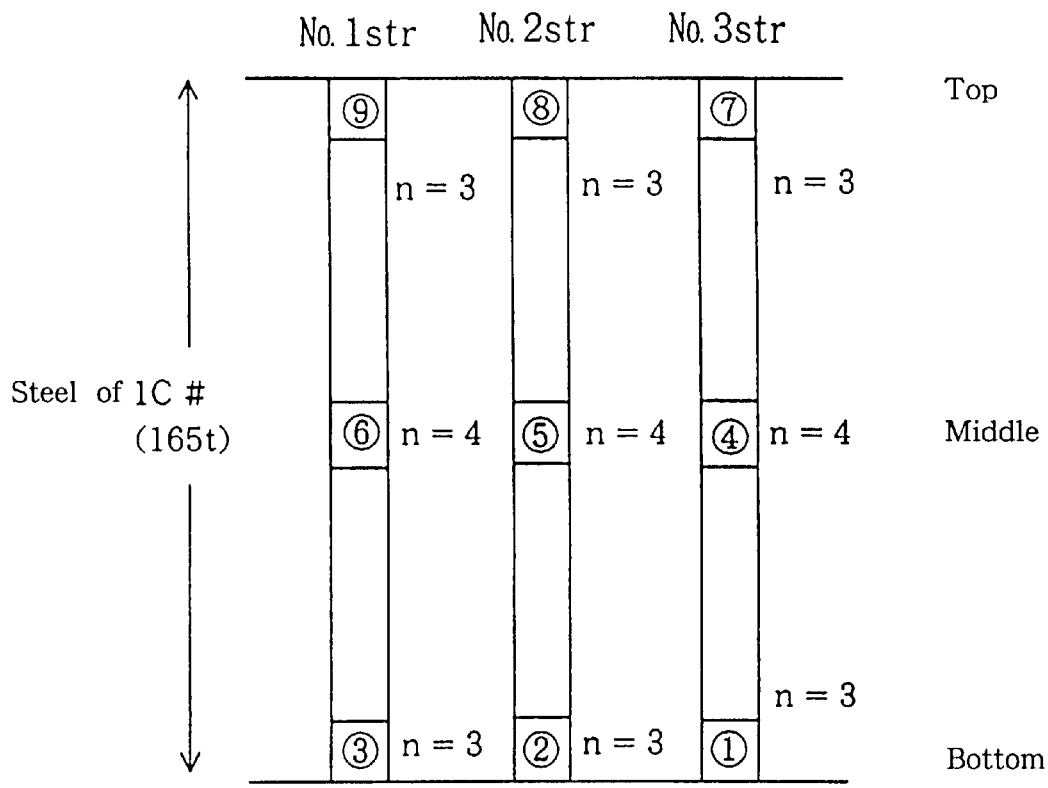
FIG. 1 shows an example of setting inspection fields in a metallic material to be tested.

The present invention described in claim 1 is a cleanliness evaluation method for metallic materials wherein cleanliness of a metallic material to be tested is evaluated by setting n inspection fields in predetermined portions of the metallic material to be tested, scanning each inspection field by ultrasonic flaw detection method for non-metallic inclusion in the metal to determine maximum non-metallic inclusion diameter $a_j$ (j=1,n), and calculating estimated maximum non-metallic inclusion diameter $a_{max}$ in the metallic material to be tested, by following equations (1) and (1') from the maximum non-metallic inclusion diameter $a_j$ (j=1,n) that has been determined for each inspection field.

[Equation 1] Linear regression of maximum non-metallic inclusion diameter $a_j$ (j=1,n) and reduced variate $y_j$ (j=1,n)

$$a = ty + u \quad (1)$$

where n=Number of tests

Reduced variate $y_j = -\ln[-\ln\{j/(n+1)\}]$ (j=1, n)

t=Regression coefficient u=Constant

[Equation 1'] Formula to calculate the maximum non-metallic inclusion diameter $a_{max}$ included in the metallic material to be tested $$a_{max} = t \times y_{max} + u \quad (1')$$

$V_0$=Reference volume of test (mm³)

V=Subject volume of estimate (mm³)

T (Return period)=$(V+V_0)/V_0$ $y_{max}$ (Reduced variate)=$-\ln[-\ln\{(T-1)/T\}]$ The present inventors reached a conclusion that, as large non-metallic inclusions greater than 20 μm are becoming less likely to be included in metallic materials and sizes of the non-metallic inclusions are also decreasing, practically it is almost impossible to detect large inclusions that occur accidentally or with an extremely low probability by methods employing microscopic observation. It was supposed that such large inclusions do not necessarily appear on the surface being inspected, but are hidden from observation.

Thus the methods employing microscopic observation for evaluating the cleanliness and assuring the quality of metallic materials was considered to be inferior in quick processing and practically incapable of adapting to the mass production processes.

Through investigations, the inventors arrived at the idea of using the ultrasonic flaw detection method, particularly that employing a focused high-frequency type device. The ultrasonic flaw detection method is basically a nondestructive inspection method, and has such advantages as the ability to test roughly prepared samples, test a large volume and carry out a quick test.

By employing the ultrasonic flaw detection method, it is made possible to test metallic materials of volumes from 1000 to several tens of thousands of times that which can be processed by the conventional methods for the sizes of non-metallic inclusions (for example, oxide, nitride, sulfide, etc.) included therein.

The present invention is characterized in that n inspection fields to be subjected to ultrasonic flaw detection are set in stated portions of the metallic material to be tested.

The inspection field refers to a location (position) in a metallic material to be tested that is scanned during ultrasonic flaw detection. Setting n inspection fields means that scanning of ultrasonic is carried out on n points of the metallic material to be tested. For example, test pieces may be taken out of n locations of the metallic material to be tested, thereby to carry out ultrasonic scanning on the n test pieces, or ultrasonic scanning may be done directly on the metallic material to be tested at the n locations.

The inspection fields are set at such positions of the tested material where large non-metallic inclusions are most likely to occur in consideration of the nature thereof, for example, in the top, middle and bottom portions of a continuously cast steel strip as shown in FIG. 1. When ultrasonic scanning is to be done after taking test pieces, it is preferable to take a plurality of (for example, three) test pieces of the same shapes from locations of the material such as top, middle and bottom portions. This makes it possible to efficiently test the metallic material to be tested as a whole. When the inspection fields (inspection samples) are set in all of the top, middle and bottom portions of the metallic material to be tested, it is also made possible to test the portions of the material that correspond to the early, intermediate and final phases of the casting process, respectively.

As for the number of inspection fields n, reliable evaluation will be carried out when n is 20 or greater in the case of a metallic material having less variations in the properties. For the convenience of statistic computations, n is preferably in a range from 30 to 60. The upper limit may be determined in consideration of the work load.

The magnitude of area to be scanned in the ultrasonic flaw detection of each inspection field (inspection sample) can be, for example, in a range from 1.0×1.0 mm² at the minimum to 700×700 mm² at the maximum. Depth of flaw detection is usually from about 0.1 mm to 5 mm (average depth is about 1 mm).

Thus assuming the method of the present invention is applied to normal scanning area of (20 to 100 mm)×(20 to 100 mm)=400 to 10000 mm²/piece and number of inspection fields (inspection samples) n=30 to 60, then the inspection field scanned per charge is from 12000 to 600000 mm²/charge, and the volume to be scanned, calculated by multiplying these figures by 100 and the number of layers in consideration of the depth of scan, is from 1,200,000 to 60,000,000 mm³/charge. Compared to the inspected area covered by the conventional method of optical microscope, that is 1000 mm³/charge at the maximum, the method of the present invention has 1000 to several tens of thousands of times greater testing capability.

According to the present invention, the next step is to determine the maximum non-metallic inclusion diameter $a_j$ (j=1,n) for each of the inspection fields described above. The maximum non-metallic inclusion diameter $a_j$ may be determined by such methods as testing n pieces taken from different inspection fields of the material or dividing a single large test piece.

The method for determining the maximum non-metallic inclusion diameter $a_j$ (j=1,n) for each inspection field or test piece may be either to compare different sets of ultrasonic echo amplitude data to find the maximum value of the ultrasonic echo amplitude data and determine the maximum non-metallic inclusion diameter by calculating on the maximum value of the ultrasonic echo amplitude data, or to calculate the non-metallic inclusion diameter data $D_i$ from the ultrasonic echo amplitude data and find the maximum non-metallic inclusion diameter from among the non-metallic inclusion diameter data $D_i$.

Then estimated maximum non-metallic inclusion diameter $a_{max}$ in the metallic material to be tested is calculated with the equations (1) and (1') from the maximum non-metallic inclusion diameter $a_j$ (j=1,n) determined as described above for each inspection field.

The equation is used to determine the diameter of inclusion by extracting the inclusion in a steel through acid dissolution or cutting in, and observing with a microscope. Thus it is made possible to estimate the maximum non-metallic inclusion diameter $a_{max}$ in the entire metallic material to be tested very accurately from the data of a part of the metallic material to be tested by relating the inclusion diameter to the ultrasonic echo amplitude.

The invention described in claim 2 is the cleanliness evaluation method for metallic materials according to claim 1 wherein the maximum non-metallic inclusion diameter $a_j$ (j=1,n) in each inspection field is determined by taking a plurality of maximum non-metallic inclusion diameters for each inspection field and rejecting abnormal values from these data.

The abnormal value herein refers to data caused by reflection from a void that is not a non-metallic inclusion, random reflection noise due to extraneous signal or the like, that can be distinguished from normal values by the waveform. While such abnormal value occur quite frequently when it is cold, error can be usually avoided by taking, for example, five pieces of non-metallic inclusion diameter data from each inspection field.

Thus such an advantage can be obtained that data from other defects than inclusion can be rejected.

The invention described in claim 3 is the cleanliness evaluation method for metallic materials according to claim 1 or 2 wherein the non-metallic inclusion diameter is determined by converting the data of amplitude of ultrasonic echo received from the non-metallic inclusions.

According to a research conducted by the present inventor, it is found that the non-metallic inclusion diameter $a_n$ and the value of ultrasonic echo amplitude C are related by the following equation. This has made it possible to carry out consistent data handling with a computer, thus enabling it to process a large amount of data, and carry out the evaluation of cleanliness of metallic materials at a high speed with a high accuracy.

Non-metallic inclusion diameter $a_n$=p×(Ultrasonic echo amplitude C)+q  (4)

where p and q are constants.

The invention described in claim 4 is the cleanliness evaluation method for metallic materials according to claim 3 wherein the non-metallic inclusion diameter is determined by calculation using a calibration curve that represents the relationship between ultrasonic echo amplitude and non-metallic inclusion diameters.

Figure 2:
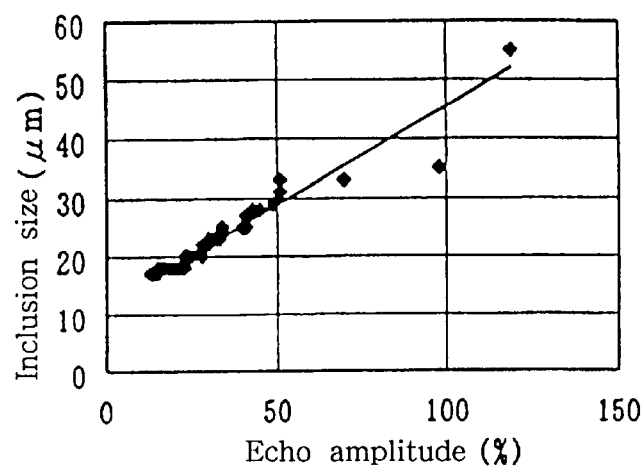
FIG. 2 shows a calibration curve representing the relation between the ultrasonic echo amplitude reflected on a non-metallic inclusion and non-metallic inclusion diameter.

The calibration curve refers to a mathematical expression or a graph that represents the relation between the echo amplitude from an inclusion in a metallic material observed with each probe in advance and the inclusion diameter determined by extracting the inclusion in the metallic material by acid dissolution or the like. An example of calibration curve is shown in FIG. 2.

The present inventors studied to develop a calibration curve for determining the inclusion diameter from a value of ultrasonic echo amplitude. In the meantime, he identified the conditions under which the echo amplitude from an inclusion can be stably determined by observing the echo amplitude from an inclusion in the metallic material to be tested with a high-frequency probe (20 to 150 MHz) in advance. Thus it is made possible to develop an accurate expression (calibration curve) that represents the relation between the ultrasonic echo amplitude and the inclusion diameter (FIG. 2), by dissolving the same sample in an acid without changing the appearance of the inclusion, then measuring the inclusion diameter by extracting the inclusion and observing it with a microscope.

Expression of regression (example)

y=0.34x+11.85 (Coefficient of correlation r=0.96)

The invention described in claim 5 is the cleanliness evaluation method for metallic materials according to claim 3 or 4 wherein the maximum non-metallic inclusion diameter $a_j$ (j=1,n) in each inspection field is determined by scanning each inspection field by ultrasonic flaw detection method for non-metallic inclusion in the metal to obtain the data of ultrasonic echo amplitude from each non-metallic inclusion, taking the maximum value among the ultrasonic echo amplitude data and calculating the maximum non-metallic inclusion diameter $a_j$ (j=1,n) from the maximum value of the ultrasonic echo amplitude data.

Since there is a correlation between the non-metallic inclusion diameter and the ultrasonic echo amplitude data obtained from the non-metallic inclusion as described above, maximum value determined from among the ultrasonic echo amplitude data of the non-metallic inclusions gives the ultrasonic echo amplitude data of the non-metallic inclusion of the largest size. Thus the maximum non-metallic inclusion diameter $a_j$ (j=1,n) may also be computed from the maximum value determined from among the data of the amplitude of ultrasonic echo received from the non-metallic inclusions.

The invention described in claim 6 is the cleanliness evaluation method for metallic materials wherein cleanliness of a metallic material to be tested is evaluated by setting n inspection fields in predetermined portions of a metallic material to be tested, scanning each inspection fields by ultrasonic flaw detection method for non-metallic inclusions in the metal to obtain ultrasonic echo amplitude data $I_j$ (j=1,n) from the maximum non-metallic inclusions in each inspection field, then calculating estimated maximum ultrasonic echo amplitude data $I_{max}$ from the estimated maximum non-metallic inclusion in the metallic material to be tested with the following equations (2) and (2') from the data $I_j$ (j=1,n) of ultrasonic echo amplitude reflected from the maximum non-metallic inclusion in each inspection field that has been determined, thereby calculating estimated maximum non-metallic inclusion diameter from the estimated maximum ultrasonic echo amplitude data $I_{max}$.

[Equation 2] Linear regression of ultrasonic echo amplitude data $I_j$ (j=1,n) from the maximum non-metallic inclusion and reduced variate $y_j$ (j=1,n)

$$I=t\times y+u \quad (2)$$

where n=Number of tests
Reduced variate $y_j=-\ln[-\ln\{j/(n+1)\}]$ (j=1, n)
t=Regression coefficient
u=Constant

[Equation 2'] Formula to calculate the maximum ultrasonic echo amplitude data $I_{max}$ from estimated maximum non-metallic inclusion in the metallic material to be tested (Expression of regression)

$$I_{max}=t \times y_{max}+u \quad (2')$$

$V_0$=Reference volume of test (mm$^3$)
$V$=Subject volume of estimate (mm$^3$)
$T$ (Return period)=$(V+V_0)/V_0$
$y_{max}$ (Reduced variate)=$-\ln[-\ln\{(T-1)/T\}]$ Since there is a correlation between the non-metallic inclusion diameter and the data of amplitude of ultrasonic echo received from the non-metallic inclusion as described above, estimated maximum non-metallic inclusion diameter may also be calculated from the estimated maximum ultrasonic echo amplitude data $I_{max}$ after calculating the maximum ultrasonic echo amplitude data $I_{max}$ that corresponds to the estimated maximum non-metallic inclusion diameter in the metallic material to be tested with the equation described above from the ultrasonic echo amplitude data obtained from the non-metallic inclusions.

The invention described in claim 7 is the cleanliness evaluation method for metallic materials according to any of claims 3 to 6 wherein the ultrasonic echo amplitude data are corrected for the depth by the following equation (3).
[Equation 3]

Corrected echo amplitude data B=(Ultrasonic echo amplitude data A)/(Depth correction factor fd)  (3)

where fd=$1+ad+bd^2$
d=Distance between focal point and the inclusion in the metal ($|d|\leq e$)
a, b and e are constants.

Figure 3:
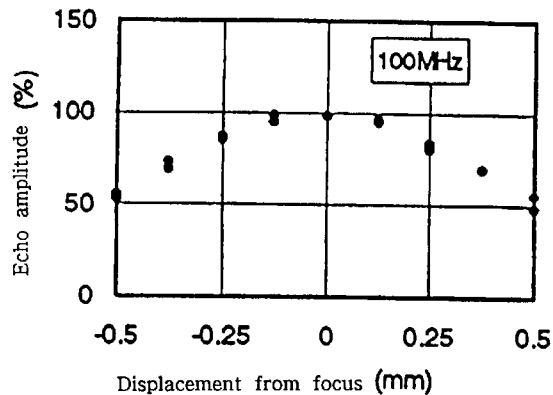
FIG. 3 shows the relation between the displacement from the focal point and the ultrasonic echo amplitude during ultrasonic flaw detection with a focused high-frequency probe.

When implementing the method of the present invention, in case the inclusion is located more distant or nearer than the position of focus, it is found that the ultrasonic echo amplitude from the inclusion decreases (FIG. 3). This may impair the accuracy of the method of the present invention.

In order to solve this problem, the present inventors have developed a method of introducing a formula of correcting the echo amplitude for the distance (FIG. 3). This further improved the accuracy of the method of the present invention.

Plots in FIG. 3 can be represented by the following equation.

$$fd=1-0.032667d-1.9675d^2$$

The invention described in claim 8 is the cleanliness evaluation method for metallic materials according to any of claims 1 to 7 wherein scanning for the non-metallic inclusion in metal by ultrasonic flaw detection method is carried out after preparing inspection samples by cutting pieces from part or all of the inspection fields.

It is made possible to carry out repetitive continuous tests and automatic measurement of n pieces, by taking inspection samples by cutting the inspection fields, especially by standardizing the length, width and thickness of the inspection samples.

The inspection samples to be taken by cutting preferably have such a configuration that allows it to test all sections including the periphery, central portion and an intermediate portion therebetween in the metallic material to be tested. With such a configuration, it is made possible to efficiently test the worst portion of the non-metallic inclusion.

The central portion is generally located at the final solidification point where much inclusions are discharged into the concentrated molten steel and much inclusions settle. Consequently, by testing all sections including this portion, detection ratio for large inclusions can be improved drastically and, as a result, accuracy of the cleanliness evaluation can be greatly improved.

Thickness of the test piece for a narrow steel strip or a sheet may be determined by giving consideration to including the center, the characteristics of the probe (range of flaw detection in the direction of depth), insensitive portion of the surface on the incident side, thickness of effective flaw detection width and vicinity of the opposite side (bottom side).

The invention described in claim 9 is the cleanliness evaluation method for metallic materials according to any of claims 1 to 8 wherein the test pieces are forged before being scanned by the ultrasonic flaw detection method for the non-metallic inclusions in the metal in each inspection field.

There may be such a case where a metallic material as cast cannot be tested due to numerous microscopic voids included therein that cause random reflections. Thus there is a problem of numerous random reflections and noises occur during scanning by the ultrasonic flaw detection method. When the object to be tested is forged before scanning with ultrasonic, the voids are crashed and diminish so that the inclusions can be tested.

The invention described in claim 10 is the cleanliness evaluation method for metallic materials according to any of claims 1 to 9 wherein a focused high-frequency probe is employed for the probe used in the ultrasonic flaw detection method.

The present invention has an object of accurately detecting microscopic inclusions. It was found that use of a focused high-frequency probe has such a remarkable effect that resolution of about a quarter wavelength can be obtained in comparison to half wavelength with that of the conventional flat type.

It is preferable to set the pitch of flaw detection to one half or less of the effective diameter of the ultrasonic beam at the focal point of the focused high-frequency probe. While it is made possible to determine the beam width at the focal point of the probe by using a test piece that includes artificial microscopic defects, setting the pitch to one half the beam width makes it possible to eliminate missing detection of inclusions. Concretely, for the accurate measurement of the inclusion diameter considering the focus point and the echo attenuation and the like, it is preferable that the pitch of flaw detection is made to be less than or equal to 30 μm and it is more preferable that it is made to be 5–10 μm.

The invention described in claim 11 is the cleanliness evaluation for metallic materials method according to any of claims 1 to 10 wherein surface roughness $R_{max}$ of the material whereon ultrasonic is applied is set to 5.0 μm or less.

A research on the method of the present invention using the ultrasonic flaw detection method showed that it is preferable to make the surface roughness $R_{max}$ of the material within 5.0 μm in consideration of the attenuation of the ultrasonic and noise prevention.

While there is no limitation to the method for making the surface roughness $R_{max}$ of the material within 5.0 μm, wet polishing of the material surface, for example, may be employed.

When implementing the method of calculating the estimated maximum non-metallic inclusion diameter $a_{max}$ from the maximum non-metallic inclusion diameter $a_j$ (j=1,n), and the method of calculating the estimated non-metallic inclusion diameter from the ultrasonic echo amplitude data $I_j$ (j=1,n), it is preferable that the subject volume of estimate V and the reference volume of test $V_0$ satisfy the following conditions.

$$30 \leq V/V_0 \leq 10000 \qquad \text{[Inequality i]}$$

$$1 \leq V_0 \leq 400000 \qquad \text{[Inequality ii]}$$

(V and $V_0$ are measured in the unit of mm$^3$.)

Figure 6:
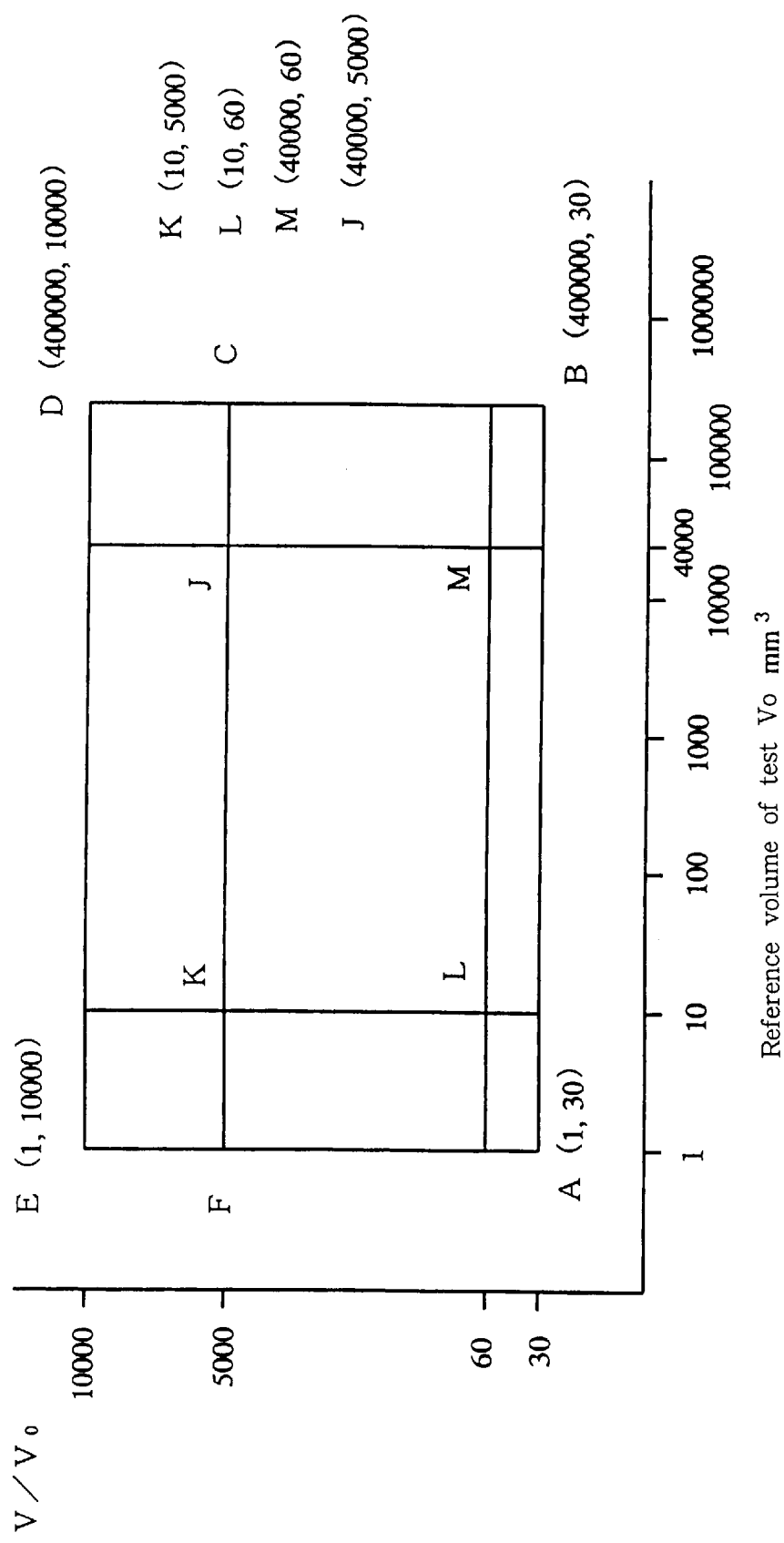
FIG. 6 shows the region defined by the inequalities (i) and (ii).

That is, ratio of the volume of metallic material where the estimation is done to the reference volume of test ($V/V_0$) is set in the range defined by the boundaries of the inequality (i) and the value of the reference volume of test $V_0$ is set in the range defined by the inequality (ii). The region defined by the inequalities (i) and (ii) is shown in FIG. 6.

While the cleanliness evaluation method according to the present invention is applied to the inside of the region ABDE defined by the inequalities (i) and (ii), upper limit of $V/V_0$ is preferably less than or equal to 5000 and lower limit of $V/V_0$ is preferably greater than or equal to 60. Upper limit of $V_0$ is preferably less than or equal to 40000, and lower limit of $V_0$ is preferably greater than or equal to 10. Maximum inclusion diameter in the metallic material can be accurately estimated, when the values of $V/V_0$ and $V_0$ are in the region ADBE defined by the inequalities (i) and (ii), or more preferably within the regions between the upper limits and the lower limits of $V/V_0$ and $V_0$ described above. Test pieces that fall in the region ABDE, or more preferably in the region between the upper limits and the lower limits described above, are easy to handle in the ultrasonic flaw detection operation. Thus accurate estimate can be made for a metallic material of large volume due to the reference volumes of test that fall in a range that is easy to handle, achieving a high efficiency of test. Meanwhile the region of $V/V_0<30$ (region below line AB in FIG. 6) is the domain of proved data where there is not much necessity to make estimate. In the region of $V_0>400000$ (region on the right side of line BD), the reference volume of test is too large for the volume to be estimated and measurement is extremely difficult. In the region $V/V_0>10000$ (region above line DE), accuracy of estimated volume may decrease. Also in the region $V_0<1$ (region on the left of line AE), the volume is too small for the test piece subjected to ultrasonic flaw detection, and the accuracy of detecting inclusions may decrease.

Volumes of steel in the region defined by the inequalities (i) and (ii) can be converted to weights as shown in Table 1.

TABLE 1

Relation of reference volume of test $V_0$ and ratio of reference volume of test to subject volume of estimate ($V/V_0$): (Comparison of converted weight)

| | $V_0$ | | | |
|---|---|---|---|---|
| | 1 mm$^3$ | 10 mm$^3$ | 40000 mm$^3$ | 400000 mm$^3$ |
| $V/V_0$ | | | | |
| Reference 1 | 0.008 g | 0.078 g | 314 g | 3.14 kg |
| 10000 | 78.5 g | 785 g | 3140 kg | 31400 kg |
| 5000 | 39.25 g | 392.5 g | 1570 kg | 15700 kg |
| 100 | 0.785 g | 7.85 g | 31.4 kg | 314 kg |
| 30 | 0.236 g | 2.36 g | 9.42 kg | 94.2 g |

The estimation method according to the present invention can be applied to a wide variety of metallic materials including Mg alloys, Al alloys, Ti alloys, Cr alloys, Fe alloys, Co alloys, Ni alloys, Cu alloys, Zn alloys, Ag alloys and Au alloys. Among these, the method is preferably applied to such materials as Fe alloys and Ni alloys, and more preferably to aluminum killed steel and other steel or alloy that contains aluminum added thereto for the purpose of suppressing the bubble generation and deoxidizing to decrease the oxygen content that causes the generation of inclusions. More specifically, the evaluation method of the present invention is preferably applied to such materials as highly clean aluminum killed steel that contains $Al \geq 0.005$ wt %.

The present invention also provides metallic materials having high accuracy and high reliability based on the cleanliness evaluation method of the present invention.

The invention described in claim 14 is metallic materials affixed with evaluation of cleanliness thereof that is given according to the estimated maximum non-metallic inclusion diameter $a_{max}$ for the entire metallic material to be tested, that is calculated with the following equations (1) and (1') from maximum non-metallic inclusion diameter $a_j$ (j=1,n) that is obtained by scanning, with the ultrasonic flaw detection method, each of n inspection fields that are set in predetermined portions of the metallic material.

[Equation 1] Linear regression of maximum non-metallic inclusion diameter $a_j$ (j=1,n) and reduced variate $y_j$ (j=1,n)

$$a = ty + u \qquad (1)$$

where n=Number of tests

Reduced variate $y_j = -\ln[-\ln\{j/(n+1)\}]$ (j=1, n)

t=Regression coefficient u=Constant

[Equation 1'] Formula to calculate the maximum non-metallic inclusion diameter $a_{max}$ included in the entire metallic material to be tested (equation of regression line)

$$a_{max} = t \times y_{max} + u \qquad (1')$$

$V_0$=Reference volume of test (mm$^3$)

V=Subject volume of estimate (mm$^3$)

T (Return period)=$(V+V_0)/V_0$ $y_{max}$ (Reduced variate)=$-\ln[-\ln\{(T-1)/T\}]$ A metallic material according to the present invention is affixed with a statement of evaluation, for example, as shown below given on the basis of the estimated maximum non-metallic inclusion diameter determined by the cleanliness evaluation method of the present invention.

TABLE 2

| Item | Condition Value/Output Value |
|---|---|
| Reference volume of test (mm$^3$) | 3800 |
| Number of tests (n) | 30 |
| Subject volume of estimate (mm$^3$) | 270000 (Corresponds to 2120 g of steel.) |
| Estimated maximum inclusion diameter ($\mu$m) | 30.3 |

The invention described in claim 15 is the metallic material affixed with the evaluation of cleanliness thereof that is given according to the estimated maximum non-metallic inclusion diameter that is determined from the estimated maximum ultrasonic echo amplitude $I_{max}$ for the entire metallic material that is calculated with the following equations (2) and (2') from maximum value data $I_j$ (j=1,n) of ultrasonic echo received from non-metallic inclusions in each of the n inspection fields that are set in predetermined portions of the metallic material.

[Equation 2] Linear regression of ultrasonic echo amplitude data $I_j$ (j=1,n) received from the maximum non-metallic inclusion and reduced variate $y_j$ (j=1, n)

$$I = ty + u \qquad (2)$$

where n=Number of tests reduced variate $y_j = -\ln[-\ln\{j/(n+1)\}]$ (j=1, n)

t=Regression coefficient u=Constant

[Equation 2'] Formula to calculate the maximum ultrasonic echo amplitude data $I_{max}$ received from estimated maximum non-metallic inclusion in the entire metallic material $$I_{max} = t \times y_{max} + u \qquad (2')$$

$V_0$=Reference volume of test (mm³)

V=Subject volume of estimate (mm³)

T (Return period)=$(V+V_0)/V_0$ $y_{max}$ (Reduced variate)=$-\ln[-\ln\{(T-1)/T\}]$ For the cleanliness evaluation given to the metallic materials according to the present invention, various forms of evaluation can be employed as exemplified above in the description of the cleanliness evaluation of the present invention.

[Embodiments]

Now preferred embodiments of the present invention will be described in detail below. While the description of the preferred embodiments takes steel as an example, the evaluation method according to the present invention is not limited to the embodiments that follow.

Embodiment 1

1. Metallic material to be tested and preparation thereof

Pieces of round steel rod shape taken from 165-ton ingots of high-carbon Cr bearing steel (for rod/pipe) as shown in FIG. 1 manufactured in continuous casting process were used as the metallic material to be tested, and cleanliness evaluation was conducted thereon according to the embodiment of the present invention.

Three or four inspection fields were set in each of portions ① through ⑨ of the round rod steel pieces shown in FIG. 1, and were forged with a forging ratio of 9. Total of 30 test pieces (inspection samples) measuring 70×70×12 mm were cut out of the inspection fields. Wet polishing was applied to the surface of each test piece to obtain surface roughness of $R_{max} \leq 4.0$ μm. The surface area of 70×70 mm was scanned for each of the test pieces measuring 70×70×12 mm prepared as described above.

2. Collection of test data

Figure 4:
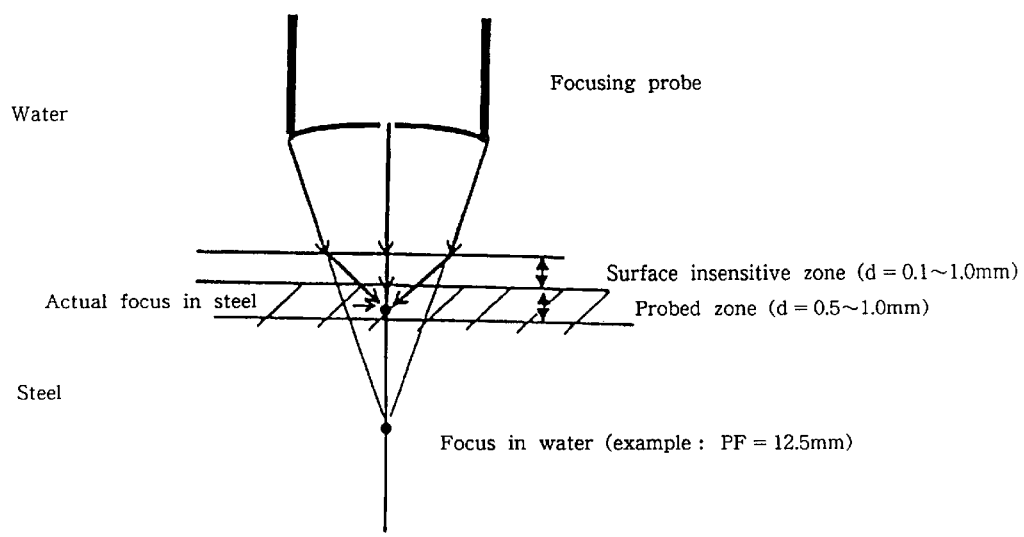
FIG. 4 is a schematic diagram showing the operation of ultrasonic flaw detection with the focused high-frequency probe.

Of the test pieces prepared as described above, a portion of 62×62 mm excluding the peripheral portion of 4 mm from the edge on the scanning surface was designated the measuring area. Flaw detection test was conducted to detect inclusions existing in a range of depth about 1.0 mm around a depth of about 1.5 mm. While the probe was scanning a portion corresponding to the reference area, ultrasonic was emitted and the echo amplitude was measured. The measured data was corrected with a factor for correcting the echo amplitude for the distance (FIG. 3) and recorded. In the ultrasonic flaw detection, a focused probe operating at 50 to 125 MHz was used. FIG. 4 schematically shows the setup of ultrasonic flaw detection.

Among the ultrasonic echo amplitude values collected on each test piece, largest five values were evaluated individually, and sets of data were obtained each comprising echo amplitude from inclusion (%), detecting position (x, y and z coordinates), characteristic of the reflection (whether the waveform is inverted or not, namely distinction of void and inclusion). The results are shown in Table 3.

[Table 3] An example of data collection (Largest five values are recorded.)

TABLE 3

An example of data collection (Largest five values are recorded.)

| Order of measurement | Maximum reflection wave height $a^n$, Detecting position (x, y and z coordinates), Inclusion or void | | | | |
|---|---|---|---|---|---|
| Measuring field | NO. 1 | NO. 2 | NO. 3 | NO. 4 | NO. 5 |
| 1 | $a_1$ (x,y,z,i/v) | $b_1$ (x,y,z,i/v) | $c_1$ (x,y,z,i/v) | $d_1$ (x,y,z,i/v) | $e_1$(x,y,z,i/v) |
| 2 | $a_2$ (x,y,z,i/v) | $b_2$ (x,y,z,i/v) | $c_2$ (x,y,z,i/v) | $d_2$ (x,y,z,i/v) | $e_2$(x,y,z,i/v) |
| 3 | $a_3$ (x,y,z,i/v) | $b_3$ (x,y,z,i/v) | $c_3$ (x,y,z,i/v) | $d_3$ (x,y,z,i/v) | $e_3$(x,y,z,i/v) |
| 4 | $a_4$ (x,y,z,i/v) | $b_4$ (x,y,z,i/v) | $c_4$ (x,y,z,i/v) | $d_4$ (x,y,z,i/v) | $e_4$(x,y,z,i/v) |
| 5 | $a_5$ (x,y,z,i/v) | $b_5$ (x,y,z,i/v) | $c_5$ (x,y,z,i/v) | $d_5$ (x,y,z,i/v) | $e_5$(x,y,z,i/v) |
| 6 | $a_6$ (x,y,z,i/v) | $b_6$ (x,y,z,i/v) | $c_6$ (x,y,z,i/v) | $d_6$ (x,y,z,i/v) | $e_6$(x,y,z,i/v) |
| . | . | . | . | . | . |
| . | . | . | . | . | . |
| . | . | . | . | . | . |
| n − 1 | $a_{n-1}$ (x,y,z,i/v) | $b_{n-1}$ (x,y,z,i/v) | $c_{n-1}$ (x,y,z,i/v) | $d_{n-1}$ (x,y,z,i/v) | $e_{n-1}$(x,y,z,i/v) |
| n | $a_n$ (x,y,z,i/v) | $b_n$ (x,y,z,i/v) | $c_n$ (x,y,z,i/v) | $d_n$ (x,y,z,i/v) | $e_n$(x,y,z,i/v) |

In the actual process, the test piece was scanned by designating a start point while dividing the C scope screen. computed data were organized in a work sheet and stored in memory. The five sets of data collected include reserve data used in checking the measured data to see whether they are normal or not, and obtain the most probable value.

After obtaining the most probable value for each inspection field, the maximum ultrasonic echo amplitude was determined for each inspection field.

Then from the maximum echo amplitude of each inspection field, the maximum non-metallic inclusion diameter $a_j$ (j=1,n) was determined using the calibration curve (relation between echo amplitude from inclusion and inclusion diameter).

3. Estimation of maximum non-metallic inclusion diameter in metallic material to be tested Estimated maximum non-metallic inclusion diameter $a_{max}$ was determined from among the maximum non-metallic inclusion diameters $a_j$ (j=1,n) of the 30 test pieces (inspection fields) obtained as described above.

The values of maximum non-metallic inclusion diameter a, that were determined using the calibration curve from the most probable value of the maximum echo amplitude of every test piece (inspection field) obtained by rejecting abnormal values caused by surface wave echo or voids, were arranged in increasing order and defined as $a_1, a_2, \ldots, a_j$, with a1 being the least value.

Figure 5:
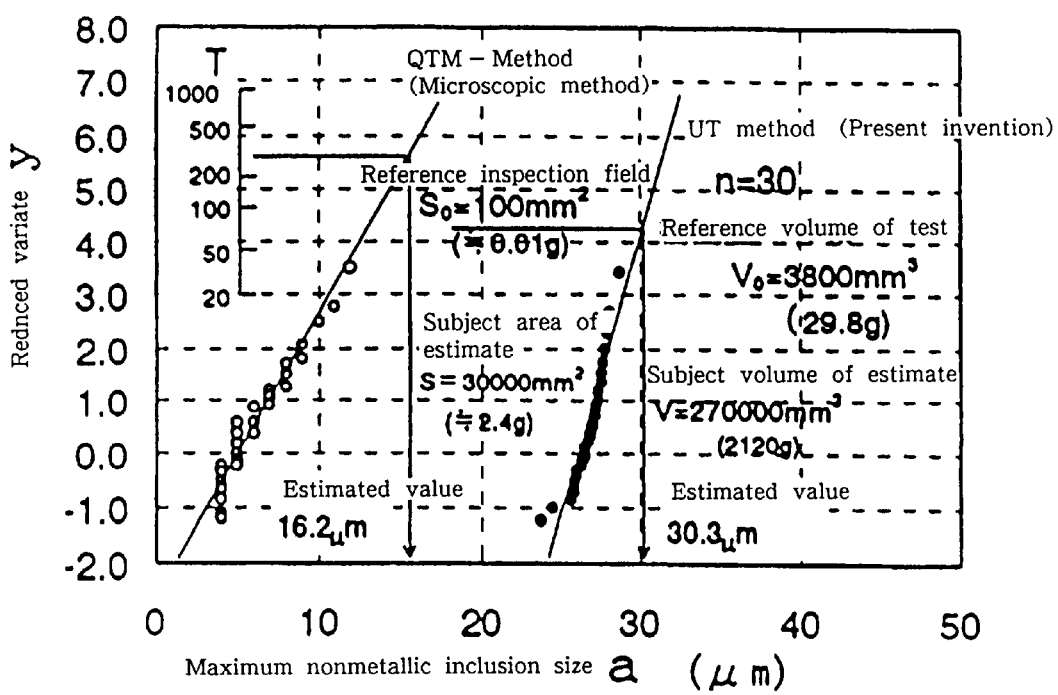
FIG. 5 compares the optical microscopic method (prior art) and the method of the present invention in estimating the maximum inclusion diameter.

The logarithm of the logarithm of the number representing the order of the test piece, 1, 2, 3, ..., j, is the reduced variate $y_j$ mentioned in the note to the equation (1). Some of the values of j, $a_j$ and $y_j$ are shown in Table 4. Test results are represented by ● in FIG. 5 while plotting the inclusion diameter along the abscissa and the reduced variate along the ordinate. The straight line that rises to the right on the right in FIG. 5 shows the linear regression of the plots.

[Table 4] Linear regression table for calculating maximum inclusion (example)

TABLE 4

Linear regression table for calculating maximum inclusion (example)

| No. | Standardization variable $y_j$ | $a_j$ (j = 1,n) (μm) |
|---|---|---|
| 1 | −1.2337 | 23.7 |
| 2 | −1.0083 | 24.5 |
| 3 | −0.8482 | 25.6 |
| 4 | −0.7167 | 25.8 |
| 5 | −0.6013 | 25.8 |
| 6 | −0.4961 | 25.9 |
| 7 | −0.3975 | 25.9 |
| 8 | −0.3035 | 26.0 |
| 9 | −0.2125 | 26.2 |
| 10 | −0.1235 | 26.4 |
| 11 | −0.0355 | 26.4 |
| 12 | 0.0523 | 26.5 |
| 13 | 0.1404 | 26.5 |
| 14 | 0.2295 | 26.7 |
| 15 | 0.3203 | 26.8 |
| 16 | 0.4134 | 26.9 |
| 17 | 0.5095 | 27.0 |
| 18 | 0.6095 | 27.0 |
| 19 | 0.7143 | 27.1 |
| 20 | 0.8250 | 27.1 |
| 21 | 0.9430 | 27.2 |
| 22 | 1.0702 | 27.3 |
| 23 | 1.2090 | 27.3 |
| 24 | 1.3628 | 27.5 |
| 25 | 1.5366 | 27.5 |
| 26 | 1.7379 | 27.6 |
| 27 | 1.9794 | 27.8 |
| 28 | 2.2849 | 27.9 |
| 29 | 2.7077 | 28.0 |
| 30 | 3.4176 | 28.7 |

*Nos. in the left column of Table 4 indicate the order of data $a_j$ obtained from the measurement of a test piece, being arranged increasing order.

Since the inspected field (hence the volume, as the same thickness is given) is the same for all test pieces in the ultrasonic flaw detection test, the reduced variate along the ordinate represents the area (namely the volume) of the test piece. In the case of Table 4, $y_j$=−1.2337 represents the reference volume of one test piece, and therefore means 62×62×1.0 mm$^3$ (=$V_0$) (approximately 29.8 g), and $y_j$=−1.0083 corresponds to the reference volume of two test pieces, 2$V_0$. Table 4 shows the maximum inclusions in each test piece arranged in the increasing order. Extreme-value distribution of these data drawn on probability paper is shown in FIG. 5. The reduced variate y along the ordinate can be obtained by taking the logarithm of the logarithm of the cumulative distribution (probability) of the test pieces for linearization. In order to estimate the maximum inclusion diameter $a_{max}$ in a region of a given volume V, an inclusion diameter that corresponds to volume V may be read from the scale of the ordinate (reduced variate) based on the straight line of the reduced variate y that has been determined. The value of $y_{max}$ that is the reduced variate for the subject volume V of estimate can be determined from the return period T (=(V+$V_0$)/$V_0$). This conversion is given by the equation (1'). The value on the ordinate that corresponds to the subject volume V of estimate is taken for the value of T (return period) described in the note to the equation (1').

In the case of FIG. 5, for example, for the volume of 270,000 mm$^3$ where estimate is to be done, maximum inclusion diameter of 30.3 μm is given by the straight line shown on the right. Volume of 270,000 mm$^3$ translates to a mass of 2.12 kg. Assuming that a thickness of about 1.0 mm is measured in the ultrasonic flaw detection, it can be said that maximum inclusion diameter in an area of 520 mm square are investigated. The return period T gives the average number of observations required to detect the inclusion diameter being required or larger ones.

4. Cleanliness evaluation for metallic material to be tested

Evaluation of cleanliness of a metallic material to be tested is given in terms of the estimated maximum inclusion diameter $a_{max}$ reference volume of test $V_0$ mm$^3$ and subject volume of estimate Vmm$^3$.

In this embodiment, evaluation of cleanliness of the metallic material to be tested, that is a round rod steel ingot, is given as the estimated maximum inclusion diameter $a_{max}$=30.3 μm, reference volume of test $V_0$=3,800 mm$^3$ and subject volume of estimate V=270,000 mm$^3$. Thus the high-carbon Cr bearing steel affixed with the evaluation of the estimated maximum inclusion diameter as described above was obtained.

In a test to detect inclusions by the acid dissolution extracting method conducted on the same metallic material of volume 270,000 mm$^3$ as that used in this embodiment, the estimated maximum inclusion diameter was 35.0 μm. Thus high accuracy of the evaluation method and the metallic material according to the present invention was verified.

Embodiment 2

150 tons of spring steel (JIS SUP10) was melted in an electric furnace. After RH degassing, the material was subjected to continuous casting to form into a bloom having a cross section of 380×490 mm. By blooming, 2-ton billets 167 mm in diameter were obtained. By rolling the billet, valve springs 5 mm in diameter were manufactured. The spring broke during operation. Observation of the fracture surface showed the existence of an inclusion having a size of 60 μm.

From the rest of the rolled material, after making the springs therefrom, test pieces not subjected to the spring making process were made. The test pieces were prepared, subjected to ultrasonic flaw detection and evaluated similarly to the first embodiment. As a result, it was estimated that the maximum inclusion diameter that could exist in the rolled steel of about 2 tons (V=0.255×10$^9$ mm$^3$) used of making the springs was 63 μm. In the case of the second embodiment, V/$V_0$=0.255×10$^9$/3800=67105. Thus it has been verified that the method according to the present invention is suited for evaluating the maximum inclusion in steel materials weighing 1 kg or more, particularly steel materials weighing 1 ton or more. Also it has been verified that the cleanliness evaluation method according to the present invention is capable of accurately evaluating the cleanliness of steel of $V_0$=3800 mm$^3$ and V/$V_0$=67105.

Embodiment 3

A high-carbon Cr bearing steel affixed with evaluation of estimated maximum inclusion diameter was obtained under the same conditions as those of the first embodiment, except that maximum values $I_j$ (j=1,n) of reflected ultrasonic were obtained by ultrasonic flaw detection method and the cleanliness was evaluated by the equations (2) and (2').

Embodiment 4

JIS SCM steel (Al content of 0.025%) was used as the metallic material to be estimated.

Estimated maximum non-metallic inclusion diameter was determined under the same conditions as Embodiment 1, except for the material described above. (Accordingly, $V_0$=3800 mm$^3$, V=270000 mm$^3$, V/$V_0$≈71.053.) Also the maximum inclusion diameter obtained by acid dissolution of the test pieces was measured.

The results are shown in Table 5.
[Table 5]

TABLE 5

SCM steel with Al content of 0.025% (Unit:μm)

| Sample No. | Estimated maximum inclusion diameter A | Maximum inclusion diameter B extracted by acid dissolution | Difference Δ = B − A |
|---|---|---|---|
| | Condition | | |
| | n = 30 Reference volume of test $V_0$ = 3800 mm³ Subject volume of estimate = 270000 mm³ $V/V_0$ ≠ 71.053 | Acid volume − dissolved V = 270000 mm³ (≠2120 g) | |
| 1 | 39.4 | 44 | 5 |
| 2 | 60.5 | 70 | 9 |
| 3 | 80.9 | 75 | −6 |
| 4 | 45.4 | 57 | 12 |
| 5 | 74.1 | 84 | 10 |
| 6 | 62.3 | 59 | −3 |
| 7 | 70.2 | 75 | 5 |
| 8 | 52.4 | 60 | 8 |
| 9 | 40.1 | 35 | −5 |
| Mean value | | | 3.9 |
| σ n − 1 | | | 6.8 |

*Sample Nos. given in the left column of Table 5 indicate the sample Nos. assigned to nine different samples.

Embodiment 5

Figure 7:
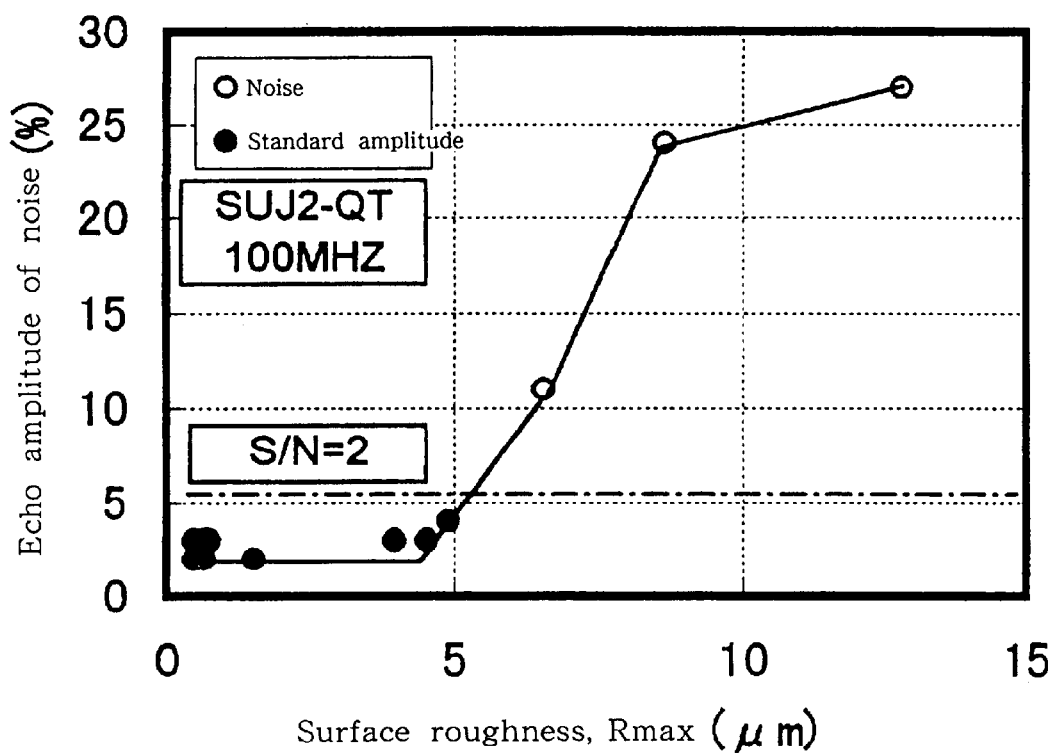
FIG. 7 shows the relation between surface roughness $R_{max}$ and echo amplitude.

The relation between surface roughness $R_{max}$ and echo amplitude was researched. The result is shown in FIG. 7. As shown in FIG. 7, where $R_{max}$ is less than or equal to 5 μm, the value of S/N is less than 2, namely the noise reflection from the surface of the test piece was not found.

$R_{max}$ was measured according to JIS B 0601-1994 (JIS: Japanese Industrial Standards. $R_{max}$ in this specification refers to $R_y$ in JIS B 0601-1994. This standard corresponds to ISO 468-1982, ISO 3274-1975).

Embodiment 6

Figure 8:
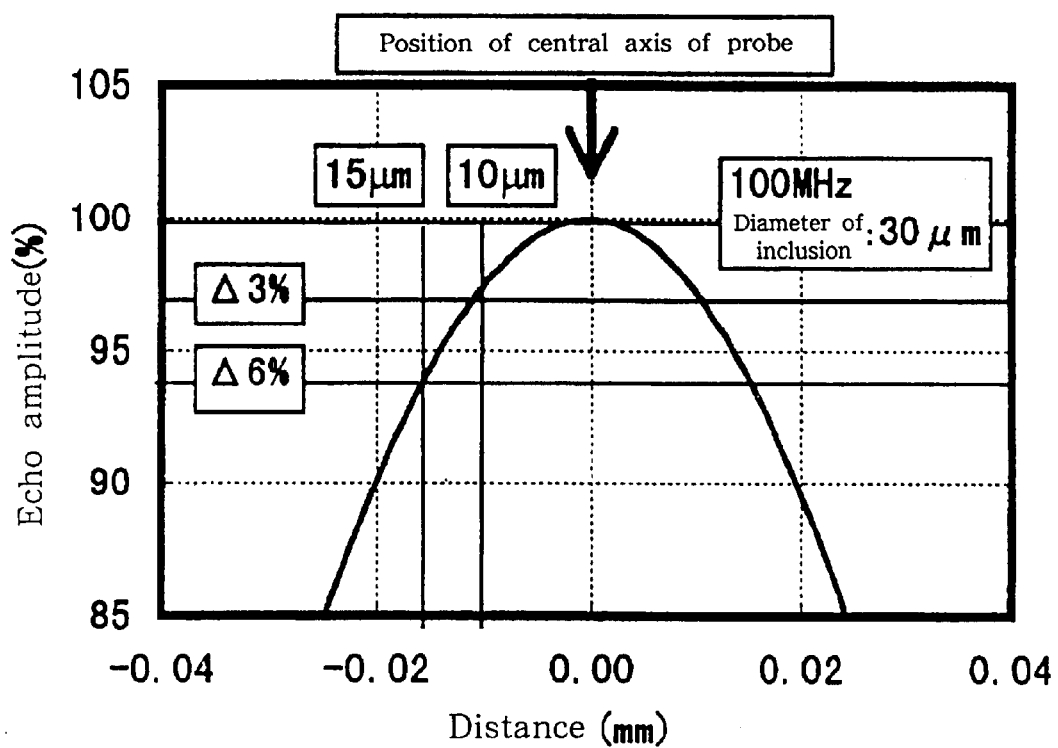
FIG. 8 shows the echo shape received from an inclusion in the test piece.

The echo shape received from an inclusion in the test piece was shown in FIG. 8.

Depending on the expression based on the calibration curve shown in FIG. 2, approximately, 6% of echo amplitude corresponds to 2 mm of inclusion diameter. So, in case demanding the accuracy of 1–2 mm size, the difference of echo amplitude from peak (maximum position) need to be kept less than about 6 point. FIG. 8 shows that it is especially preferable that the scanning pitch is made to be less than or equal to 10 μm.

According to the present invention, cleanliness of metallic materials can be evaluated quickly with high accuracy and high reliability.

Also the present invention, in compliance with the remarkable improvement in the cleanliness of metallic materials such as steel recently achieved, contributes the increasing requirements for the evaluation of cleanliness and quality assurance of the metallic materials, and is very useful in meeting the needs of the industry. For users of metallic materials who apply mechanical processing to the metallic materials and manufacture mechanical parts, improvement in the accuracy of estimating the diameters of inclusions in the material is desirable in that the accuracy of estimating the strength of the parts in the design phase can be improved resulting in improved reliability of the parts. This makes it possible to reduce the parts in size and weight as required, without setting excessively high safety factors.

While there has been described what are at present considered to be preferred embodiments of the invention, it will be understood that various modifications may be made thereto, and it is intended that the appended claims cover all such modifications as fall within the true spirit and scope of the invention.

What is claimed is:

1. A cleanliness evaluation method for metallic materials characterized in that cleanliness of a metallic material to be tested is evaluated by setting n inspection fields in predetermined portions of a metallic material to be tested, scanning each inspection field by ultrasonic flaw detection method for non-metallic inclusion in the metal thereby to determine maximum non-metallic inclusion diameter $a_j$ (j=1, n), and calculating estimated maximum non-metallic inclusion diameter $a_{max}$ in the metallic material to be tested, by the following equations (1) and (1') from the maximum non-metallic inclusion diameter $a_j$ (j=1,n) that has been determined for each inspection field;

[Equation 1] Linear regression of maximum non-metallic inclusion diameter $a_j$ (j=1,n) and reduced variate $y_j$ (j=1,n), $$a = ty + u \quad (1),$$

where n=Number of tests,
Reduced variate $y_j = -\ln[-\ln\{j/(n+1)\}]$ (where J=1, n),
t=Regression coefficient,
u=Constant,

[Equation 1'] Formula to calculate the estimated maximum non-metallic inclusion diameter $a_{max}$ included in the metallic material to be tested (equation of regression line), $$a_{max} = t \times y_{max} + u \quad (1'),$$

$V_0$=reference volume of test (mm³),
V=Subject volume of estimate (mm³),
T (Return period)=$(V+V_0)/V_0$,
$y_{max}$ (Reduced variate)=$-\ln[-\ln\{(T-1)/T\}]$.

2. A cleanliness evaluation method for metallic materials according to claim 1 wherein the maximum non-metallic inclusion diameter $a_j$ (j=1,n) in each inspection field is determined by taking a plurality of non-metallic inclusion diameters of larger values for each inspection field and rejecting abnormal values from these data.

3. A cleanliness evaluation method for metallic materials according to claim 1 wherein the non-metallic inclusion diameter is determined by converting the data of amplitude of ultrasonic echo received from the non-metallic inclusion.

4. A cleanliness evaluation method for metallic materials according to claim 3 wherein the non-metallic inclusion diameter is determined by calculation using a calibration curve that represents the relationship between ultrasonic echo amplitude and non-metallic inclusion diameters.

5. A cleanliness evaluation method for metallic materials according to claim 3 wherein the maximum non-metallic inclusion diameter $a_j$ (j=1,n) in each inspection field is determined by scanning each inspection field by ultrasonic flaw detection method for non-metallic inclusion in the metal to obtain the ultrasonic echo amplitude data from each non-metallic inclusion, taking the maximum value among the ultrasonic echo amplitude data and calculating the maximum non-metallic inclusion diameter $a_j$ (j=1,n) from the maximum value of the ultrasonic echo amplitude data.

6. A cleanliness evaluation method for metallic materials characterized in that cleanliness of a metallic material to be tested is evaluated by setting n inspection fields in predetermined portions of a metallic material to be tested, scanning each inspection field by ultrasonic flaw detection method for non-metallic inclusion in the metal to obtain ultrasonic echo amplitude data $I_j$ (j=1,n) received from the maximum non-metallic inclusion in each inspection field, then calculating estimated maximum ultrasonic echo amplitude data $I_{max}$ from the estimated maximum non-metallic inclusion in the metallic material to be tested with the following equations (2) and (2') from the data $I_j$ (j=1, n) of ultrasonic echo amplitude reflected from the maximum non-metallic inclusion in each inspection field that has been determined, thereby calculating estimated maximum non-metallic inclusion diameter from the estimated maximum ultrasonic echo amplitude data $I_{max}$;

[Equation 2] Linear regression of ultrasonic echo amplitude data $I_j$ (j=1, n) from the maximum non-metallic inclusion and reduced variate $y_j$ (j=1,n), $$I=ty+u \quad (2),$$

where n=Number of tests,

Reduced variate $y_j=-\ln[-\ln\{j/(n+1)\}]$ (where j=1, n), t=Regression coefficient, u=Constant,

[Equation 2'] Formula to calculate the maximum ultrasonic echo amplitude data $I_{max}$ from estimated maximum non-metallic inclusion in the metallic material to be tested, $$I_{max}=t \times y_{max}+u \quad (2'),$$

$V_0$=Reference volume of test (mm$^3$),

V=Subject volume of estimate (mm$^3$),

T (Return period)=$(V+V_0)/V_0$, $y_{max}$ (Reduced variate)=$-\ln[-\ln\{(T-1)/T\}]$.

7. A cleanliness evaluation method for metallic materials according to claim 6 wherein the ultrasonic echo amplitude data are corrected for the depth by the following Equation (3);

[Equation 3]

$$\text{Corrected ultrasonic echo amplitude data B=(Ultrasonic echo amplitude data A)/(Depth correction factor fd)} \quad (3)$$

where $fd=1+ad+bd^2$, d=Distance between focal point and the inclusion in the metal ($|d| \leq e$), a, b and e are constants.

8. A cleanliness evaluation method for metallic materials according to claim 1 wherein scanning for the non-metallic inclusion in metal by ultrasonic flaw detection method is carried out after preparing inspection samples by cutting pieces from part or all of the inspection fields.

9. A cleanliness evaluation method for metallic materials according to claim 1 wherein test pieces are forged before being scanned by the ultrasonic flaw detection method for non-metallic inclusion in the metal in each inspection field.

10. A cleanliness evaluation method for metallic materials according to claim 1 wherein a focused high-frequency probe is employed for a probe used in the ultrasonic flaw detection.

11. A cleanliness evaluation method for metallic materials according to claim 1 wherein surface roughness $R_{max}$ of the material whereon ultrasonic is applied is set to 5.0 µm or less.

12. A cleanliness evaluation method for metallic materials according to claim 1 wherein $V/V_0$ and $V_0$ satisfy the following relationships [i] and [ii];

$$30 \leq V/V_0 \leq 10000, \quad \text{[Equation i]}$$

$$1 \leq V_0 \leq 400000. \quad \text{[Equation ii]}$$

13. A cleanliness evaluation method for metallic materials according to claim 1 wherein scanning for non-metallic inclusion in metal is carried out by setting the pitch of flaw detection to be less than or equal to 30 µm.

14. A metallic material affixed with evaluation of cleanliness thereof given according to estimated maximum non-metallic inclusion diameter $a_{max}$ for the entire metallic material to be tested, which is calculated with the following equations (1) and (1') from maximum non-metallic inclusion diameter data $a_j$ (j=1,n) obtained with ultrasonic flaw detection method by scanning each of n inspection fields that are set in predetermined portions of the metallic material;

[Equation 1] Linear regression of maximum non-metallic inclusion diameter $a_j$ (j=1,n) and reduced variate $y_j$ (j=1,n), $$a=ty+u \quad (1),$$

where n=Number of tests,

Reduced variate $y_j=-\ln[-\ln\{j/(n+1)\}]$ (where j=1, n), t=Regression coefficient, u=Constant,

[Equation 1'] Formula to calculate the estimated maximum non-metallic inclusion diameter $a_{max}$ included in the entire metallic material to be tested (equation of regression line), $$a_{max}=t \times y_{max}+u \quad (1'),$$

$V_0$=Reference volume of test (mm$^3$),

V=Subject volume of estimate (mm$^3$), (Return period)=$(V+V_0)/V_0$, $y_{max}$ (Reduced variate)=$-\ln[-\ln\{(T-1)/T\}]$.

15. A metallic material affixed with evaluation of cleanliness thereof that is given according to estimated maximum non-metallic inclusion diameter determined from estimated maximum ultrasonic echo amplitude $I_{max}$ for the entire metallic material that is calculated with the following equations (2) and (2') from maximum value data $I_j$ (j=1,n) of the ultrasonic echo received from non-metallic inclusion in each of n inspection fields that are set in predetermined portions of the metallic material;

[Equation 2] Linear regression of ultrasonic echo amplitude data $I_j$ (j=1, n) from the maximum non-metallic inclusion and reduced variate $y_j$ (j=1,n), $$I=ty+u \quad (2),$$

where n=Number of tests,

Reduced variate $y_j=-\ln[-\ln\{j/(n+1)\}]$ (where j=1,n), t=Regression coefficient, u=Constant,

[Equation 2'] Formula to calculate the maximum ultrasonic echo amplitude data $I_{max}$ from estimated maximum non-metallic inclusion in the entire metallic material, $$I_{max} = t \times y_{max} + u \quad (2),$$

$V_0$=Reference volume of test (mm³),
V=Subject volume of estimate (mm³),
T (Return period)=$(V+V_0)/V_0$,
$y_{max}$ (Reduced variate)=$-\ln[-\ln\{(T-1)/T\}]$.

16. A metallic material according to claim 14 wherein the number n of the inspection fields set in the predetermined portion of the metallic material is 20 or more.

17. A metallic material according to claim 14 wherein the metallic material is a highly clean steel containing Al≧0.005 wt %.

* * * * *